United States Patent [19]

Arora et al.

[11] Patent Number: 5,360,792
[45] Date of Patent: Nov. 1, 1994

[54] ANTI-PROLIFERATIVE AND ANTI-INFLAMMATORY COMPOUNDS: 5- OR 6-DEOXY HEXOSE MONOSACCHARIDES HAVING A SATURATED NITROGEN-CONTAINING HETEROCYCLE AT THE 5- OR 6-POSITION BOUND THROUGH THE NITROGEN ATOM

[75] Inventors: Sudershan K. Arora, Lansdale; David S. Thomson, Bluebell; M. Nayeem Akhtar, Lansdale, all of Pa.

[73] Assignee: Greenwich Pharmaceuticals Incorporated, Ft. Washington, Pa.

[21] Appl. No.: 905,320

[22] Filed: Jun. 29, 1992

Related U.S. Application Data

[63] Continuation-in-part of Ser. No. 810,906, Dec. 20, 1991, abandoned.

[51] Int. Cl.$^5$ .................. A01N 43/04; C07H 15/00
[52] U.S. Cl. .................... 514/23; 536/17.3; 536/18.7; 536/4.1; 514/25
[58] Field of Search ........... 536/17.3, 18.7, 4.1; 514/23, 25

[56] References Cited

U.S. PATENT DOCUMENTS

| | | | |
|---|---|---|---|
| Re. 30,354 | 7/1980 | Gordon | 536/4 |
| Re. 30,379 | 8/1980 | Gordon | 536/4 |
| Re. 32,268 | 10/1986 | Gordon | 514/25 |
| Re. 33,000 | 7/1989 | Gordon | 514/25 |
| 2,715,121 | 8/1955 | Glen et al. | 260/209 |
| 3,939,145 | 2/1976 | Gordon | 260/210 |
| 3,939,146 | 2/1976 | Gordon | 260/210 |
| 3,965,262 | 6/1976 | Gordon | 424/180 |
| 4,016,261 | 4/1977 | Gordon | 424/180 |
| 4,017,608 | 4/1977 | Gordon | 424/180 |
| 4,056,322 | 11/1977 | Gordon et al. | 536/4 |
| 4,251,520 | 2/1988 | Bruzzese et al. | 424/180 |
| 4,735,934 | 4/1988 | Gordon | 514/25 |
| 4,738,953 | 4/1988 | Gordon | 514/25 |
| 4,996,195 | 2/1991 | Ronsen et al. | 514/23 |
| 5,010,058 | 4/1991 | Ronsen et al. | 514/23 |

FOREIGN PATENT DOCUMENTS

WO92/04359 3/1992 WIPO.
WO92/14745 9/1992 WIPO.

OTHER PUBLICATIONS

Z. Ahmed et al., Synthetic Communications, 18(5), 501–505 (1988).

Primary Examiner—Johann Richter
Assistant Examiner—Joseph K. McKane
Attorney, Agent, or Firm—Finnegan, Henderson, Farabow, Garrett & Dunner

[57] ABSTRACT

The compounds of this invention are 5- or 6-deoxy hexose monosaccharides having a saturated nitrogen-containing heterocycle at the 5- or 6-position bound through the nitrogen atom. The saturated nitrogen-containing heterocycle substituent is shown by the following formula:

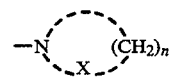

where X is $CH_2$, NH or O; and n ranges from 3–6. These hexose monosaccharides may also be ethereally substituted at least one other position. The compounds exhibit anti-proliferative and anti-inflammatory activity. Methods of preparation, pharmaceutical compositions containing the compounds and methods of treating inflammatory and/or autoimmune disorders employing the compounds are disclosed.

45 Claims, No Drawings

ANTI-PROLIFERATIVE AND ANTI-INFLAMMATORY COMPOUNDS: 5- OR 6-DEOXY HEXOSE MONOSACCHARIDES HAVING A SATURATED NITROGEN-CONTAINING HETEROCYCLE AT THE 5- OR 6-POSITION BOUND THROUGH THE NITROGEN ATOM

CONTINUING DATA

This application is a continuation-in-part of U.S. patent application Ser. No. 07/810,906, filed Dec. 20, 1991 now abandoned.

BACKGROUND OF THE INVENTION

1. Field of the Invention

This invention relates to 5- or 6-deoxy hexose monosaccharides having a saturated nitrogen-containing heterocycle at the 5- or 6-position bound through the nitrogen atom and a method for their preparation. These compounds exhibit anti-proliferative and anti-inflammatory activity and are useful for treating mammals with inflammatory and/or autoimmune disorders. This invention also relates to pharmaceutical compositions containing the disclosed compounds and to methods of treating inflammatory and/or autoimmune disorders employing the disclosed compounds.

2. Description of the Related Art

Certain monosaccharides and their derivatives are known to have therapeutic value in the treatment of inflammatory and autoimmune disorders. Monosaccharides, particularly the hexoses, are well known compounds. Synthesis of derivatives of these sugars can be accomplished by synthetic techniques which are known in the art.

To prepare derivatives of the monosaccharides it is common to block or protect one or more of the hydroxyl groups with acetal blocking groups such as isopropylidene or cyclohexylidene, and only leave one or two hydroxyl groups free to undergo further reaction. Various blocking groups, and methods are described in U.S. Pat. Nos. 2,715,121 and 4,056,322 and incorporated here by reference. For example, to prepare a derivative of α,D-glucose which is blocked in its furanose ring structure, the 1,2- and 5,6-hydroxyl groups can be blocked using an isopropylidene blocking group and the 3-position left open to undergo further reaction. After the reaction to derivatize the 3-position is complete, the blocking groups may be selectively removed to allow for further derivatization at other positions if desired.

Various derivatives of six carbon sugars, as well as synthetic methods, are described in U.S. Pat. Nos. Re. 30,354, Re. 30,379, Re. 32,268, 4,056,322, 4,735,934, 4,738,953, 4,996,195 and 5,010,058 copending U.S. patent application Ser. Nos. 07/658,311 and 07/757,817. The disclosures of these documents are incorporated here by reference. The therapeutic activity of monosaccharides and their derivatives is also disclosed in the above documents.

Two well known derivative of α,D-glucofuranose, having beneficial therapeutic properties is amiprilose, 1,2-O-isopropylidene 3-O-3'-(N,N'-dimethylamino-n-propyl)-α,D-glucofuranose, and its hydrochloric acid salt, amiprilose HCl (THERAFECTIN®). These compounds are known to have anti-inflammatory activity and demonstrated utility in managing the signs and symptoms of rheumatoid arthritis. More generally, these compounds have activity as immunomodulators, and therefore have a therapeutic effect on other autoimmune disorders such as psoriasis, eczema or lupus.

Deoxy derivatives of 1,2-O-isopropylidene-α,D-glucofuranose are described in U.S. Pat. No. 5,010,058. That patent describes methods of preparing deoxy derivatives of 1,2-O-isopropylidene-α,D-glucofuranose, and the use of such compounds in treating mammals with inflammatory and/or autoimmune deficiency disorders.

While some prior art monosaccharide derivatives have shown beneficial therapeutic activity, high doses of these monosaccharides, such as THERAFECTIN®, are often needed to be effective and produce the desired results. Because therapy for those inflammatory and autoimmune disorders is often midterm or long-term, there is a need to develop potent, nontoxic compounds which can be orally administered to promote ease of treatment and patient compliance.

An object of the present invention, therefore, is to provide new compounds that exhibit significantly greater potency than available compounds, such as THERAFECTIN®.

Other objects and advantages of the invention will be set forth in the description which follows, and in part will be apparent from the description, or may be learned by practice of the invention. The objects and advantages of the invention may be realized and obtained by means of the compounds, pharmaceutical compositions and methods of treatment pointed out in the appended claims.

SUMMARY OF THE INVENTION

To achieve the above objects, and in accordance with the purpose of the invention as embodied and broadly described here, there are provided:

5- or 6-deoxy hexose monosaccharides having a saturated nitrogen-containing heterocycle at the 5- or 6-position bound through the nitrogen atom. The saturated nitrogen-containing heterocyclic substituent of the compounds of the present invention is shown by the following formula:

where X is $CH_2$, NH or O; and n ranges from 3–6. These hexose monosaccharides may also be ethereally substituted at one or more other positions. The compounds exhibit beneficial therapeutic properties and are useful in the treatment of inflammatory and autoimmune disorders. Specifically, these compounds have demonstrated inhibitory effects on fibroblast proliferation and immunomodulatory activity in art recognized in vitro screening tests. Compounds having this activity are useful for treating animals and humans with various dermatological and/or arthritic conditions such as psoriasis, atopic dermatitis, rheumatoid arthritis, osteoarthritis, scleroderma and systemic lupus erythematosus.

The present invention also provides pharmaceutical compositions containing the subject hexose monosaccharide compounds, and methods for the treatment of inflammatory and/or autoimmune disorders employing those compounds. The pharmaceutical compositions comprise an effective amount of at least one of the subject compounds or a physiologically acceptable salt thereof with a pharmaceutically acceptable carrier.

Advantageously, the compounds of the present invention exhibit greater potency, in terms of their activity, than other known monosaccharides such as THERAFECTIN®.

DETAILED DESCRIPTION OF THE INVENTION

The compounds of this invention are 5- or 6-deoxy hexose monosaccharides having a saturated nitrogen-containing heterocycle at the 5- or 6-position bound through the nitrogen atom. The saturated nitrogen-containing heterocyclic substituent of the compounds of the present invention is shown by the following formula:

where X is $CH_2$, NH or O; and n ranges from 3-6. Preferred heterocyclic rings are selected from a pyrrolidinyl ring, a piperidinyl ring, and a morpholinyl ring.

In a preferred embodiment, the 5- or 6-deoxy hexose monosaccharide compounds of this invention are also ethereally substituted at one or more positions on the sugar. That is, one or more of the free hydroxyl groups of the monosaccharide is substituted with a substituent selected from a $C_1$-$C_{20}$ alkyl group; a $C_{13}$-$C_{20}$ alkenyl group; a $C_{13}$-$C_{20}$ alkynyl group; a $(CH_2)_m NR'R''$ group, where m ranges from 1-5, R' and R'' are each selected from H or a lower alkyl group; and an alkylaryl group. When the ether substituent is a $(CH_2)_m NR'R''$ group, m is preferably 3, R' and R'' are preferably each selected from H, methyl, ethyl or propyl, and most preferably, R' and R'' are both methyl. When the ether substituent is an alkyl group, it is preferably a $C_7$-$C_{20}$ alkyl group. A preferred alkylaryl group is a propylphenyl group.

The 5- or 6-deoxy hexose monosaccharides described here may also have as substituents which together form an acetal protecting group. Preferred acetal protecting groups are selected from an isopropylidene group and a cyclohexylidene group.

In one embodiment of the invention, the hexose monosaccharide is a 5-deoxy hexose monosaccharides where the nitrogen containing heterocycle is at the 5-position. One group of compounds within this embodiment is represented by formula I:

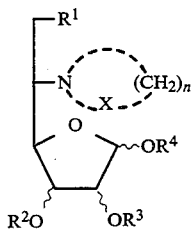

wherein
R$^1$ is H or OR$^5$ wherein R$^5$ is $C_1$-$C_{20}$ alkyl; $C_1$-$C_{20}$ alkenyl; $C_1$-$C_{20}$ alkynyl; $(CH_2)_m NR'r''$, wherein m ranges from 1-5, R' and R'' are each selected from H or a lower alkyl group; and alkylaryl;

R$^2$ is hydrogen $C_1$-$C_{20}$ alkyl; $C_1$-$C_{20}$ alkenyl; $C_1$-$C_{20}$ alkynyl; $(CH_2)_m NR'R''$, wherein m ranges from 1-5, R' and R'' are each selected from H or a lower alkyl group; and alkylaryl;

R$^3$ and R$^4$ are each H or together form an acetal protecting group;

X is $CH_2$, NH or O;

n ranges from 3-6;

or a physiologically acceptable salt thereof. The preferred substituents are those described above.

The hexose monosaccharides of formula I include hexose monosaccharides where the hexose monosaccharide is an idose or a talose.

Preferred idose compounds are:
1,2-O-Isopropylidene-5-deoxy-5-pyrrolidinyl-6-O-dodecyl-β,L-Idofuranose, (Ia);
1,2-O-Isopropylidene-5-deoxy-5-pyrrolidinyl-6-O-pentadecyl-β,L-Idofuranose, (Ib);
1,2-O-Isopropylidene-3-O-heptyl-5,6-dideoxy-5-pyrrolidinyl-β,L-Idofuranose, (Ic);
1,2-O-Isopropylidene-3-O-decyl-5,6-dideoxy-5-pyrrolidinyl-β,L-Idofuranose, (Id);
1,2-O-Isopropylidene-3-O-dodecyl-5,6-dideoxy-5-pyrrolidinyl-β,L-Idofuranose, (Ie);
1,2-O-Isopropylidene-3-O-pentadecyl-5,6-dideoxy-5-pyrrolidinyl-β,L-Idofuranose, (If); and
1,2-O-Isopropylidene-3-O-decyl-5,6-dideoxy-5-piperidinyl-β,L-idofuranose, (Ig).

Particularly preferred idose compounds are compounds Ie and If.

The 5-deoxy hexose monosaccharides of the present invention also encompass gulose compounds of formula II:

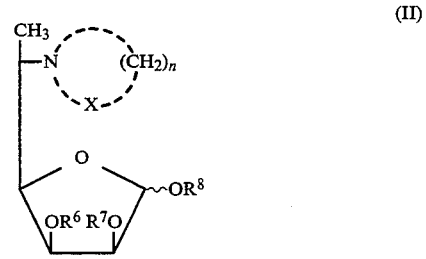

wherein
R$^6$ and R$^7$ are each H or together form an acetal protecting group;
R$^8$ is $C_1$-$C_{20}$ alkyl; $C_1$-$C_{20}$ alkenyl; $C_1$-$C_{20}$ alkynyl; $(CH_2)_m NR'R''$, wherein m ranges from 1-5, R' and R'' are each selected from H or a lower alkyl group; and alkylaryl;

X is $CH_2$, NH or O;

n ranges from 3-6;

or a physiologically acceptable salt thereof. The preferred substituent are those described above. A preferred compound according to formula II is 3-phenylpropyl 2,3-O-isopropylidene-5,6-dideoxy-5-pyrrolidinyl-β,L-gulofuranoside (IIa).

In another embodiment, the hexose monosaccharide of this invention is a 6-deoxy hexose monosaccharides where the nitrogen containing heterocycle is at the 6-position. A first group of compounds within this embodiment are compounds according to formula III:

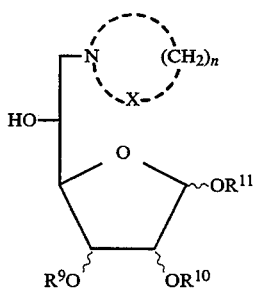

(III)

wherein $R^9$ is $C_1$–$C_{20}$ alkyl; $C_1$–$C_{20}$ alkenyl; $C_1$–$C_{20}$ alkynyl; $(CH_2)_m NR'R''$, wherein m ranges from 1–5, R' and R'' are each selected from H or a lower alkyl group; and alkylaryl;

$R^{10}$ and $R^{11}$ are each H or together form an acetal protecting group;

X is $CH_2$, NH or O;

n ranges from 3–6;

or a physiologically acceptable salt thereof. Preferred substituents are those described above.

Within the compounds embodied in formula I are those where the hexose monosaccharide is glucose and allose.

Preferred glucose compounds are:

1,2-O-Isopropylidene-3-O-heptyl-6-deoxy-6-pyrrolidinyl-α,D-glucofuranose, (IIIa);

1,2-O-Isopropylidene-3-O-decyl-6-deoxy-6-pyrrolidinyl-α,D-glucofuranose, (IIIb);

1,2-O-Isopropylidene-3-O-dodecyl-6-deoxy-6-pyrrolidinyl-α,D-glucofuranose, (IIIc);

1,2-O-Isopropylidene-3-O-pentadecyl-6-deoxy-6-pyrrolidinyl-α,D-glucofuranose, (IIId);

1,2-O-Isopropylidene-3-O-eicosyl-6-deoxy-6-pyrrolidinyl-α,D-glucofuranose, (IIIe);

1,2-O-Isopropylidene-3-O-heptyl-6-deoxy-6-piperidenyl-α,D-glucofuranose, (IIIf);

1,2-O-Cyclohexylidene-3-O-decyl-6-deoxy-6-pyrrolidinyl-α,D-glucofuranose, (IIIg);

1,2-O-Cyclohexylidene-3-O-dodecyl-6-deoxy-6-pyrrolidinyl-α,D-glucofuranose, (IIIh);

Preferred allose compounds are:

1,2-O-Isopropylidene-3-O-decyl-6-deoxy-6-pyrrolidinyl-α,D-allofuranose (IIIi); and 1,2-O-Isopropylidene-3-O-decyl-6-deoxy-6-morpholinyl-α,D-allofuranose (IIIj).

Particularly preferred compounds of formula III are compounds IIIc and IIIi.

The 6-deoxy hexose monosaccharides of the present invention also include compounds where the hexose monosaccharide is a mannose. These mannose derivatives are shown in formula IV:

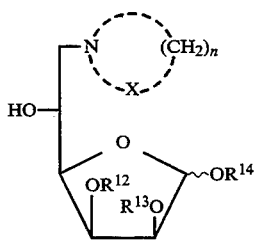

(IV)

wherein $R^{12}$ and $R^{13}$ are each H or together form an acetal protecting group;

$R^{14}$ is $C_1$–$C_{20}$ alkyl; $C_1$–$C_{20}$ alkenyl; $C_1$–$C_{20}$ alkynyl; $(CH_2)_m NR'R''$, wherein m ranges from 1–5, R' and R'' are each selected from H or a lower alkyl group; and alkylaryl;

X is $CH_2$, NH or O;

n ranges from 3–6;

or a physiologically acceptable salt thereof. Preferred substituents are those described above. Preferred compounds according to formula IV are:

3-Phenylpropyl 2,3-O-isopropylidene-6-deoxy-6-piperidinyl-α,D-mannofuranoside (IVb).

Undecyl 2,3-O-isopropylidene-6-deoxy-6-pyrrolidinyl-α,D-mannofuranoside (IVb).

The mannose compound IVb is particularly preferred.

The compounds of the invention may be prepared according to a general synthetic procedure. The examples below demonstrate the general synthetic procedure, as well as the specific preparation, for compounds according to this invention. The examples are illustrative, and are not intended to limit, in any manner, the claimed invention.

The general procedure can be described as follows. First, suitably protected hexofuranose having a free hydroxyl group is alkylated at that hydroxyl group with a base and an appropriate alkyl halide. Selective removal of a protecting group provides an intermediate which can be preferentially tosylated at either position. The resulting tosylate is then displaced upon treatment with a saturated heterocyclic amine to give the deoxy, N-heterocyclic compounds of the present invention directly. Alternatively, the tosylate could be reduced with a suitable reducing agent to yield an intermediate which, upon a second tosylation and subsequent reaction with a saturated heterocyclic amine gave a second series of dideoxy compounds such as compounds Ic-g.

According to this general procedure, the present invention also relates to a method for the preparation of cyclic amine substituted deoxy monosaccharides comprising the steps of:

1) tosylating at the hydroxyl position of the monosaccharide to be substituted; and 2) contacting the tosylated monosaccharide with a saturated cyclic amine to displace the tosylate group.

Treatment of the compounds of either of the above series with an aqueous acid removes the final protecting group and generates a third series of fully unblocked compounds. These fully unblocked monosaccharide compounds can exist in essentially three different structural forms in solution: an open chain form, and furanose; and pyranose ring structures. An equilibrium is established between these different forms, the state of which is dependent upon the specific compounds. Isolation of the compounds in one or more of these forms can be accomplished as is known in the art.

PHARMACOLOGIC ACTIVITY

The compounds of the present invention have demonstrated immunomodulatory and anti-proliferative effects in biological assays. Standard in vitro immunologic assays were performed on all compounds of the present invention in order to assess anti-proliferative and immunomodulatory activity. These included the mixed lymphocyte response (MLR), the mouse spleen cell mitogen induced blastogenesis assay and the BUD-8 cell line fibroblast proliferation assay. The MLR functions as a test of immunomodulatory effects of the compounds whereby inhibitory effects on T lymphocyte activation and antigen presentation are determined. Anti-proliferative effects were demonstrated by measuring the inhibitory effects of the compounds of the present invention on the cellular proliferation of Concanavalin A stimulated murine splenocytes and BUD-8 human fibroblasts. Because inflammation and mechanisms involved in the pathogenesis of autoimmune diseases involve cellular activation and proliferation as well as abnormal immune system activation, these assays are appropriate to use as screens for novel compounds in the treatment of inflammatory and/or autoimmune disorders.

The compounds of the present invention all demonstrated anti-proliferative and immunomodulatory activities. Concentrations tested ranged from 3 to 300 micromolar. With strong activity defined as half maximal inhibitory concentrations of less than 30 micromolar, the compounds of the present invention uniformly demonstrated strong in vitro anti-proliferative effects. Similarly, the compounds of this series were also found to be strong immunomodulators with the exception of Compound IIId which demonstrated anti-proliferative activity but weaker immunomodulatory activity. These results indicate that the compounds of the present invention are extremely highly active agents with potent in vitro activities.

The deoxy hexose derivatives of the present invention are useful for treating animals and mammals with inflammatory and/or autoimmune disorders such as psoriasis, atopic dermatitis, rheumatoid arthritis, osteoarthritis, scleroderma and systemic lupus erythematosus. Due to their valuable pharmacological properties, the compounds of the present invention or their physiologically acceptable salts are particularly suitable for use as active compounds in pharmaceutical compositions for the treatment of, for example, inflammatory rheumatic disorders.

The compounds can either be administered alone in the form of microcapsules, in mixtures with one another or in combination with acceptable pharmaceutical carriers. The invention, thus, also relates to pharmaceutical compositions which comprise an effective amount of at least one compound of the present invention with or without a pharmaceutically and physiologically acceptable carrier. If appropriate, the compound may be in the form of a physiologically acceptable salt, for example, an acid-addition salt.

The present invention also encompasses a method of treating animals or humans suffering from inflammatory and/or autoimmune disorders which comprises administering to the animal or person an effective amount of at least one of the compounds of the invention or an acid-addition salt thereof, with or without a pharmaceutically acceptable carrier. The compositions according to the invention can be administered orally, topically, rectally, internally, or, if desired, parenterally; oral administration is preferred.

Suitable solid or liquid galenic formulations are, for example, granules, powders, coated tablets, microcapsules, suppositories, syrups, elixirs, suspensions, emulsions, drops or injectable solutions. Also, the compounds may be employed in preparations having a protracted release of the active compound. Commonly used additives in protracted release preparations are excipients, disintegrates, binders, coating agents, swelling agents, glidants, or lubricants, flavors, sweeteners or solubilizers. More specifically, frequently used additives are, for example, magnesium carbonate, titanium dioxide, lactose, mannitol and other sugars, talc, lactalbumin, gelatin, starch, cellulose and its derivatives, animal and vegetable oils, polyethylene glycols and solvents. The solvents include sterile water and monohydric or polyhydric alcohols such as glycerol.

The pharmaceutical compositions are preferably produced and administered in dosage units, each unit containing as an active component an effective dose of at least one compound of the present invention and/or at least one of its physiologically acceptable salts. In the case of mammals, the effective dose to treat autoimmune and/or anti-inflammatory disorders can range from about 1 to 100 mg per kilogram of body weight per day.

EXAMPLES

NMR spectra were recorded on a Varian XL-300 MHz using TMS as the internal standard reference. FTIR spectra were recorded on a Nicolet MX-1 instrument using KBr plates. Optical rotation was measured on a Perkin-Elmer Model 241 polarimeter. CIMS were obtained with a Finnigan MAT 4510 mass spectrometer with an INCOS data system. Generally, a direct exposure probe was used and ammonia was used as a reagent gas (0.35 mm Hg, 120° C. source temperature).

EXAMPLE 1

Preparation of
1,2-O-Isopropylidene-5-deoxy-5-pyrrolidinyl-6-O-dodecyl-$\beta$,L-Idofuranose, Compound Ia Step 1: Preparation of 1,2:3,5-Di-O-Isopropylidene-6-O-dodecyl-$\alpha$,D-glucofuranose:

A mixture of 1,2:3,5-di-O-isopropylidene-$\alpha$,D-glucofuranose (10 g) and dry powdered sodium hydroxide (4,6 g) was heated at 100° C. for one hour using diminished pressure. The vacuum line was then disconnected and dodecyl bromide (11.5 g) was added. The mixture was stirred at 120° for 2 hours. The reaction flask was then cooled and added ether (150 ml), filtered through celite and washed with 150 ml more of ether. The combined ether solution was subjected to rotary evaporation and the residue obtained was purified by flash chromatography using 5% ether in hexane to yield pure compound (13.7 g, 84%).

Step 2: Preparation of 1,2-O-Isopropylidene-6-O-dodecyl-$\alpha$,D-glucofuranose:

Aqueous perchloric acid (30%, 13.7 ml) was added dropwise to a stirred solution of 1,2;3,5-di-O-isopropylidene-6-O-dodecyl-$\alpha$,D-glucofuranose (13.7 g) in THF (14 ml) at 0°–5° C. After 1 hour, a saturated solution of potassium carbonate was added until a pH of 9.0 was reached. The reaction mixture was then filtered through celite, washed with THF (100 ml), and solvent removed. The crude product was purified by flash chromatography using 10% ether in hexane. The yield of the pure product was 5.3 g (43%).

Step 3: Preparation of 1,2-O-Isopropylidene-6-O-dodecyl-5-p-tosyl-$\alpha$,D-glucofuranose:

A solution of p-toluenesulfonyl chloride (2.6 g) in pyridine (15 ml) was added dropwise to a stirred solution of 1,2-O-isopropylidene-6-O-dodecyl-$\alpha$,D-glucofuranose (5.3 g) in pyridine (15 ml) at ice bath temperature. The reaction mixture was stirred for 2.5 hours. The pyridine was then removed and the residue obtained was dissolved in ethylacetate (100 ml), washed with a saturated NaHCO$_3$ solution (2×30 ml), a saturated brine solution (2×30 ml), and the organic layer separated, dried over MgSO$_4$, filtered and solvent removed. The residue was purified by flash chromatography using 5% ether in hexane to get the title compound (2 g) in 28.5% yield.

Step 4: Preparation of 1,2-O-Isopropylidene-6-O-dodecyl-5-deoxy-5-pyrrolidinyl-β,L-Idofuranose:

A mixture of the 5-p-tosyl compound obtained in Step 3 above (2.0 g) and pyrrolidine (6 ml) was heated in an oil bath at 85° C. for 4.5 hours. It was cooled to the ambient temperature and added ether (50 ml). The ether layer was washed with a saturated NaHCO$_3$ solution (2×20 ml), a saturated brine solution (1×20 ml), dried over MgSO$_4$ and filtered. The solvent was removed from the filtrate and the residue purified by chromatography (50% ether in hexane). The yield of the pure compound was (0.9 g; 54%).

EXAMPLE 2

Preparation of 1,2-O-Isopropylidene-5-deoxy-5-pyrrolidinyl-6-O-pentadecyl-β,L-Idofuranose, Compound Ib This compound was prepared in the same manner as described in Example 1, except that the dodecylbromide was replaced by pentadecylbromide. The overall yield starting from 1,2:3,5-di-O-isopropylidene-α,D-glucofuranose was 20.02%.

EXAMPLE 3

Preparation of 1,2-O-Isopropylidene-3-O-heptyl-5,6-dideoxy-5-pyrrolidinyl-β,L-Idofuranose, Compound Ic Step 1: Preparation of 1,2-O-Isopropylidene-3-O-heptyl-6-deoxy-α,D-glucofuranose:

This compound was prepared by the same procedure as described in Example 3 of U.S. Pat. No. 5,010,058 which is incorporated here by reference.

Step 2: Preparation of 1,2-O-Isopropylidene-6-deoxy-5-p-toluenesulfonyl-3-O-heptyl-α,D-glucofuranose:

To a stirred solution of 1,2-O-isopropylidene-3-O-heptyl-6-deoxy-α,D-glucofuranose (23.7 g) in pyridine (200 ml) was added a solution of p-toluenesulfonyl chloride (12 g) in pyridine (100 ml), with stirring at room temperature for 10 hours and worked up by the same procedure as described in Step 3 of Example 1. The yield of the pure compound was 82%.

Step 3: Preparation of 1,2-O-Isopropylidene-3-O-heptyl-5,6-dideoxy-5-pyrrolidinyl-β,L-idofuranose:

This compound was obtained in 81% yield by reacting 5-tosyl compound, as obtained in Step 2 above, with pyrrolidine. The procedure used was the same as described in Step 4 of Example 1. The yield of the pure compound was 68%.

EXAMPLE 4

Preparation of 1,2-O-Isopropylidene-3-O-decyl-5,6-dideoxy-5-pyrrolidinyl-β,L-idofuranose, Compound Id This product was obtained in an overall yield of 37% by the same procedure as described in Example 3, Steps 1 through 3, except decylbromide was used in place of heptylbromide.

EXAMPLE 5

Preparation of 1,2-O-Isopropylidene-3-O-dodecyl-5,6-dideoxy-5-pyrrolidinyl-β-L-idofuranose, Compound Ie The title compound was obtained in an overall yield of 41% by using the same procedure as described in Example 4. However, dodecylbromide was used instead of decylbromide.

EXAMPLE 6

Preparation of 1,2-O-Isopropylidene-3-O-pentadecyl-5,6-dideoxy-5-pyrrolidinyl-β,L-idofuranose, Compound If The title compound was obtained in an overall yield of 35% by using the same experimental procedure as described in Example 4. However, pentadecylbromide was used in place of decylbromide.

EXAMPLE 7

Preparation of 1,2-O-Isopropylidene-3-O-decyl-5,6-dideoxy-5-piperidinyl-β,L-idofuranose, Compound Ig This compound was obtained in an overall yield of 34% by the same procedure as described in Example 3, Steps 1 through 3, except that decylbromide was substituted for heptylbromide in Step 1 and piperidine for pyrrolidine in Step 3.

EXAMPLE 8

3-Phenylpropyl 2,3-O-isopropylidene-5,6-dideoxy-5-pyrrolidinyl-β,L-gulofuranoside, Compound IIa Step 1: 3-Phenylpropyl 2,3-O-isopropylidene-6-deoxy-α,Dmannofuranoside.

This compound was synthesized in 50% yield from 3-phenylpropyl 2,3-O-isopropylidene-6-p-tosyl-α,D-mannofuranoside. The reaction conditions and procedures were the same as described in Example 3.

Step 2: 3-Phenylpropyl 2,3-O-isopropylidene-5-p-tosyl-6-deoxy-α,D-mannofuranoside.

The title compound was prepared in 60% yield by treating 3-phenylpropyl 2,3-O-isopropylidene-6-deoxy-α,D-mannofuranoside with p-toluenesulphonylchloride in pyridine as in Example 3, Step 2.

Step 3: 3-Phenylpropyl 2,3-O-isopropylidene-5,6-dideoxy-5-pyrrolidinyl-β,L-gulofuranoside (IVa).

This compound was obtained in 42% yield by reacting 3-phenylpropyl 2,3-O-isopropylidene-5-p-tosyl-6-deoxy-α,D-mannofuranoside with pyrrolidine as in Example 3, Step 3.

EXAMPLE 9

The general procedure for the synthesis of 1,2-O-Isopropylidene-3-O-alkyl-6-p-tosyl-α,D-glucofuranoses, (alkyl=C$_7$H$_{15}$) has been described in Example 3 of U.S. Pat. No. 5,010,058, and is incorporated here by reference. Other 3-O-alkyl derivatives such as C$_{10}$H$_{21}$, C$_{12}$H$_{25}$ and C$_{15}$H$_{31}$ derivatives can be prepared by substituting the appropriate alkylhalide for the 1-bromoheptane employed in Example 3 of U.S. Pat. No. 5,010,058.

EXAMPLE 10

Preparation of
1,2-O-Isopropylidine-3-O-heptyl-6-deoxy-6-pyrrolidinyl-α,D-glucofuranose, Compound IIIa A mixture of 1,2-O-isopropylidene-3-O-heptyl-6-p-tosyl-α,D-glucofuranose (1.95 g, prepared according to Example 9) and pyrrolidine (6 ml) was heated at 75°–80° C. for one hour. The excess pyrrolidine was then removed and the residue worked up by the same procedure as described for Step 4 of Example 1. The yield of the pure compound was 82%.

EXAMPLE 11

Preparation of
1,2-O-Isopropylidine-3-O-decyl-6-deoxy-6-pyrrolidinyl-α,D-glucofuranose, Compound IIIb This compound was obtained in 68% yield by treating 1,2-O-isopropylidine-3-O-decyl-6-p-tosyl-α,D-glucofuranose, (prepared according to Example 9, substituting 1-bromodecane for 1-bromoheptane), with pyrrolidine. The procedure used was the same as described for Example 10.

EXAMPLE 12

Preparation of
1,2-O-Isopropylidene-3-O-dodecyl-6-deoxy-6-pyrrolidinyl-α,D-glucofuranose, Compound IIIc The title compound was prepared in 77% yield by treating 1,2-O-isopropylidene-3-O-dodecyl-6-p-tosyl-α,D-glucofuranose (prepared according to Example 9, substituting 1-bromododecane for 1-bromoheptane), with pyrrolidine by employing the same procedure as described in Example 10.

EXAMPLE 13

Preparation of
1,2-O-Isopropylidene-3-O-pentadecyl-6-deoxy-6-pyrrolidinyl-α,D-glucofuranose, Compound IIId This compound was synthesized in 71% yield by treating 1,2-O-isopropylidene-3-O-pentadecyl-6-p-tosyl-α,D-glucofuranose, (prepared according to Example 9 substituting 1-bromopentadecane for 1-bromoheptane), with pyrrolidine. The reaction conditions and workup procedures were the same as described in Example 10.

EXAMPLE 14

Preparation of
1,2-O-Isopropylidene-3-O-eicosyl-6-deoxy-6-pyrrolidinyl-α,D-glucofuranose, Compound IIIe This compound was prepared in 47% yield by treating 1,2-O-Isopropylidene-3-O-eicosyl-6-p-tosyl-α,D-glucofuranose, (prepared according to Example 9, substituting 1-bromoelcosane for 1-bromoheptane), with pyrrolidine. The reaction conditions and workup procedures were the same as described in Example 10.

EXAMPLE 15

1,2-O-Isopropylidene-3-O-heptyl-6-deoxy-6-piperidenyl-α,D-glucofuranose, Compound IIIf This compound was prepared in 77% yield by treating 1,2-O-Isopropylidene-3-O-heptyl-6-p-tosyl-α,D-glucofuranose, (prepared according to Example 9), with piperidine. The reaction conditions and workup procedures were the same as described in Example 10.

EXAMPLE 16

1,2-O-Cyclohexylideneylidene-3-O-decyl-6-deoxy-6-pyrrolidinyl-α,D-glucofuranose, Compound IIIg 1,2-O-cyclohexylidene-3-O-decyl-6-p-tosyl-α,D-glucofuranose was prepared according to the procedure used in Example 5 of U.S. Pat. No. 5,010,058 substituting 1,2:5,6-di-O-cyclohexylidene-α,D-glucofuranose for 1,2:5,6-di-O-isopropylidene-α,D-glucofuranose.

The title compound was synthesized in 70% yield by treatment of 1,2-O-cyclohexylidene-3-O-dodecyl-6-p-tosyl-α,D-glucofuranose prepared as in Example 9 with pyrrolidine.

EXAMPLE 17

1,2-O-Cyclohexylidene-3-O-dodecyl-6-deoxy-6-pyrrolidinyl-α,D-glucofuranose, Compound IIIh 1,2-O-cyclohexylidene-3-O-dodecyl-6-p-tosyl-α,D-glucofuranose was prepared according to the procedure used in Example 5 of U.S. Pat. No. 5,010,058 substituting 1,2:5,6-di-O-cyclohexylidene-α,D-glucofuranose for 1,2:5,6-di-O-isopropylidene-α,D-glucofuranose and 1-bromododecane for 1-bromoheptane.

The title compound was synthesized in 75% yield by treatment of 1,2-O-cyclohexylidene-3-O-dodecyl-6-p-tosyl-α,D-glucofuranose prepared as in Example 16 with pyrrolidine.

EXAMPLE 18

Preparation of
1,2-O-Isopropylidene-3-O-decyl-6-deoxy-6-pyrrodidinyl-α,D-allofuranose, Compound IIIi The title compound was prepared in 21% overall yield from 1,2:5,6-Di-O-isopropylidene-α,D-allofuranose (J. D. Stevens, Methods in Carbohyd. Chem., VI, 123 (1972)) as in Example 10.

EXAMPLE 19

Preparation of
1,2-O-Isopropylidene-3-O-decyl-6-deoxy-6-morpholinyl-α,D-allofuranose, Compound IIIj This title compound was synthesized in 20% overall yield from 1,2:5,6-Di-O-isopropylidene-α,D-allofuranose as in Example 18.

EXAMPLE 20

Preparation of 3-phenylpropyl 2,3-O-isopropylidene-6-deoxy-6-piperidinyl-α,D-mannofuranoside, Compound IVa Step 1: Preparation of 2,3:5,6-Di-O-isopropylidene-α,D-mannofuranose.

A mixture of D-mannose (60 g), acetone (1000 ml) and concentrated sulphuric acid (5 g) were stirred at room temperature for 24 hrs. The reaction mixture was neutralized with solid K$_2$CO$_3$, then filtered and the filtrate concentrated. The crude reaction mixture thus obtained was chromatographed on silica gel using 1:1 diethylether-hexane to give the title compound in 56% yield.

Step 2: 3-Phenylpropyl 2,3:5,6-Di-O-isopropylidene-α,D-mannofuranoside.

To a solution of 2,3:5,6-Di-O-isopropylidene-α,D-mannuforanoside (20 g) and phenylpropylbromide (18.4 g) in DMF (50 ml) was added sodium hydride (2.2 g).

The resultant mixture was heated to 35° C. for 3 hours at which time the reaction was quenched with methanol (20 ml) then water (10 ml). The crude mixture was concentrated under vacuum and the residue obtained dissolved in ether (200 ml), filtered and washed with water. The organic phase was dried over magnesium sulphate, filtered and concentrated. The crude material was purified by silica gel chromatography using 15% diethylether in hexane. The title compound was obtained in 50% yield.

Step 3: 3-Phenylpropyl 2,3-D-Isopropylidene-α,D-mannofuranoside.

The title compound was synthesized as in Step 2, Example 1, in 60% yield.

Step 4: 3-Phenylpropyl 2,3-O-isopropylidene-6-p-tosyl-α,D-mannofuranoside.

This compound was synthesized as in Example 9 in 35% yield.

Step 5: Preparation of 3-Phenylpropyl 2,3-O-isopropylidene-6-deoxy-6-piperidinyl-α,D-mannofuranoside, (IIa).

The title compound was prepared as in Example 10 in 20% overall yield.

EXAMPLE 21

Preparation of Undecyl 2,3-O-isopropylidene-6-deoxy-6-pyrrolidinyl-α,D-mannofuranoside, Compound IVb This compound was prepared from Undecyl 2,3-O-isopropylidene-6-p-tosyl-α,D-mannofuranoside in 34% overall yield. The reaction conditions and workup procedures were the same as described in Example 10.

We claim:

1. A hexofuranose monosaccharide of formula I:

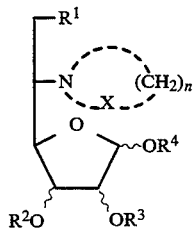

(I)

wherein
R$^1$ is H or OR$^5$ wherein R$^5$ is C$_1$–C$_{20}$ alkyl; C$_3$–C$_{20}$ alkenyl; C$_3$–C$_{20}$ alkynyl; (CH$_2$)$_m$NR'R", wherein m ranges from 1–5, R' and R" are each selected from H or a lower alkyl group; or R$^5$ is alkylaryl;
R$^2$ is hydrogen, C$_1$–C$_{20}$ alkyl; C$_3$–C$_{20}$ alkenyl; C$_3$–C$_{20}$ alkynyl; (CH$_2$)$_m$NR'R", wherein m ranges from 1–5, R' and R" are each selected from H or a lower alkyl group; or R$^2$ is alkylaryl;
R$^3$ and R$^4$ are each H or together form an acetal protecting group;
X is CH$_2$, NH or O;
n ranges from 3–6;
or a physiologically acceptable salt thereof.

2. The hexofuranose monosaccharide of claim 1, wherein the heterocyclic ring is selected from a pyrrolidinyl ring, a piperidinyl ring, and a morpholinyl ring.

3. The hexofuranose monosaccharide of claim 2, wherein R$^1$ is H and R$^2$ is a C$_7$–C$_{20}$ alkyl or a propylphenyl group.

4. The hexofuranose monosaccharide of claim 3, wherein R$^3$ and R$^4$ together form an acetal protecting group selected from an isopropylidene group and a cyclohexylidene group.

5. The hexofuranose monosaccharide of claim 3, wherein the hexofuranose monosaccharide is an idose.

6. The hexofuranose monosaccharide of claim 5, wherein the hexose monosaccharide is selected from
1,2-O-Isopropylidene-5-deoxy-5-pyrrolidinyl-6-O-dodecyl-β,L-Idofuranose;
1,2-O-Isopropylidene-5-deoxy-5-pyrrolidinyl-6-O-pentadecyl-β,L-Idofuranose;
1,2-O-Isopropylidene-3-O-heptyl-5,6-dideoxy-5-pyrrolidinyl-β,L-Idofuranose;
1,2-O-Isopropylidene-3-O-decyl-5,6-dideoxy-5-pyrrolidinyl-β,L-Idofuranose;
1,2-O-Isopropylidene-3-O-dodecyl-5,6-dideoxy-5-pyrrolidinyl-β,L-Idofuranose;
1,2-O-Isopropylidene-3-O-pentadecyl-5,6-dideoxy-5-pyrrolidinyl-β,L-Idofuranose; and
1,2-O-Isopropylidene-3-O-decyl-5,6-dideoxy-5-piperidinyl-β,L-idofuranose.

7. A hexofuranose monosaccharide of formula II:

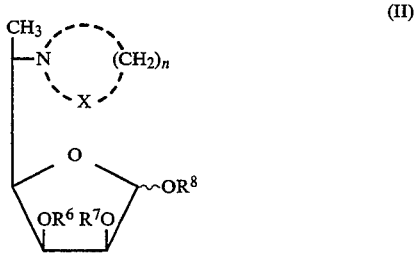

(II)

wherein
R$^6$ and R$^7$ are each H or together form an acetal protecting group;
R$^8$ is C$_1$–C$_{20}$ alkyl; C$_3$–C$_{20}$ alkenyl; C$_3$–C$_{20}$ alkynyl; (CH$_2$)$_m$NR'R", wherein m ranges from 1–5, R' and R" are each selected from H or a lower alkyl group; or alkylaryl;
X is CH$_2$, NH or O;
n ranges from 3–6;
or a physiologically acceptable salt thereof.

8. The hexofuranose monosaccharide of claim 7, wherein the heterocyclic ring is selected from a pyrrolidinyl ring, a piperidinyl ring, and a morpholinyl ring.

9. The hexofuranose monosaccharide of claim 8, wherein R$^8$ is a C$_7$–C$_{20}$ alkyl or a propylphenyl group.

10. The hexofuranose monosaccharide of claim 9, wherein R$^6$ and R$^7$ together form an acetal protecting group selected from an isopropylidene group and a cyclohexylidene group.

11. The hexofuranose monosaccharide of claim 10, wherein the hexofuranose monosaccharide is 3-Phenylpropyl 2,3-O-isopropylidene-5,6-dideoxy-5-pyrrolidinyl-β,L-gulofuranoside.

12. A hexofuranose monosaccharide of formula III:

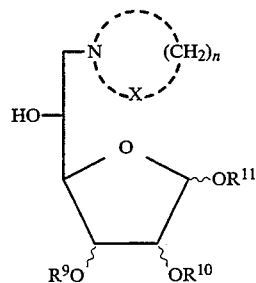

(III)

wherein
$R^9$ is $C_1$-$C_{20}$ alkyl; $C_3$-$C_{20}$ alkenyl; $C_3$-$C_{20}$ alkynyl; $(CH_2)_mNR'R''$, wherein m ranges from 1-5, R' and R'' are each selected from H or a lower alkyl group; or alkylaryl;

$R^{10}$ and $R^{11}$ are each H or together form an acetal protecting group;

X is $CH_2$, NH or O;

n ranges from 3-6;

or a physiologically acceptable salt thereof.

13. The hexofuranose monosaccharide of claim 12, wherein the heterocyclic ring is selected from a pyrrolidinyl ring, a piperidinyl ring, and a morpholinyl ring.

14. The hexofuranose monosaccharide of claim 13, wherein $R^9$ is a $C_7$-$C_{20}$ alkyl or a propylphenyl group.

15. The hexofuranose monosaccharide of claim 14, wherein $R^{10}$ and $R^{11}$ together form an acetal protecting group selected from an isopropylidene group and a cyclohexylidene group.

16. The hexofuranose monosaccharide of claim 14, wherein the hexose monosaccharide is glucose.

17. The hexofuranose monosaccharide of claim 16, wherein the hexose monosaccharide is selected from
1,2-O-Isopropylidene-3-O-heptyl-6-deoxy-6-pyrrolidinyl-α,D-glucofuranose;
1,2-O-Isopropylidene-3-O-decyl-6-deoxy-6-pyrrolidinyl-α,D-glucofuranose;
1,2-O-Isopropylidene-3-O-dodecyl-6-deoxy-6-pyrrolidinyl-α,D-glucofuranose;
1,2-O-Isopropylidene-3-O-pentadecyl-6-deoxy-6-pyrrolidinyl-α,D-glucofuranose;
1,2-O-Isopropylidene-3-O-eicosyl-6-deoxy-6-pyrrolidinyl-α,D-glucofuranose;
1,2-O-Isopropylidene-3-O-heptyl-6-deoxy-6-piperidinyl-α,D-glucofuranose;
1,2-O-Cyclohexylidene-3-O-decyl-6-deoxy-6-pyrrolidinyl-α,D-glucofuranose; and
1,2-O-Cyclohexylidene-3-O-dodecyl-6-deoxy-6-pyrrolidinyl-α,D-glucofuranose.

18. The hexofuranose monosaccharide of claim 14, wherein the hexofuranose monosaccharide is allose.

19. The hexofuranose monosaccharide of claim 18, wherein the hexose monosaccharide is selected from
1,2-O-Isopropylidene-3-O-decyl-6-deoxy-6-pyrrolidinyl-α,D-allofuranose; and
1,2-O-Isopropylidene-3-O-decyl-6-deoxy-6-morpholinyl-α,D-allofuranose.

20. A hexofuranose monosaccharide of formula IV:

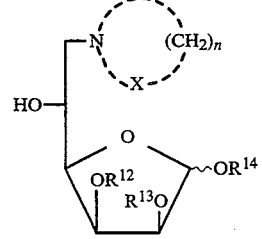

(IV)

wherein
$R^{12}$ and $R^{13}$ are each H or together form an acetal protecting group;
$R^{14}$ is $C_1$-$C_{20}$ alkyl; $C_3$-$C_{20}$ alkenyl; $C_3$-$C_{20}$ alkynyl; $(CH_2)_mNR'R''$, wherein m ranges from 1-5, R' and R'' are each selected from H or a lower alkyl group; or alkylaryl;
X is $CH_2$, NH or O;
n ranges from 3-6;
or a physiologically acceptable salt thereof.

21. The hexofuranose monosaccharide of claim 20, wherein the heterocyclic ring is selected from a pyrrolidinyl ring, a piperidinyl ring, and a morpholinyl ring.

22. The hexofuranose monosaccharide of claim 21, wherein $R^{14}$ is a $C_7$-$C_{20}$ alkyl or a propylphenyl group.

23. The hexofuranose monosaccharide of claim 22, wherein $R^{12}$ and $R^{13}$ together form an acetal protecting group selected from an isopropylidene group and a cyclohexylidene group.

24. The hexofuranose monosaccharide of claim 22, wherein the hexofuranose monosaccharide is 3-phenylpropyl 2,3-O-isopropylidene-6-deoxy-6-piperidinyl-α,D-mannofuranoside.

25. The hexofuranose monosaccharide of claim 22, wherein the hexofuranose monosaccharide is undecyl 2,3-O-isopropylidene-6-deoxy-6-pyrrolidinyl-α,D-mannofuranoside.

26. A pharmaceutical composition comprising a compound according to claim 20 and a pharmaceutically acceptable carrier.

27. A method of treating an animal or human suffering from an inflammatory and/or autoimmune disorder comprising administering thereto an amount effective to treat an inflammatory and/or autoimmune disorder of the compound according to claim 20.

28. The method of claim 27, wherein said administration is oral administration.

29. The method of claim 27, wherein said administration is parental administration.

30. A pharmaceutical composition comprising a compound according to claim 12 and a pharmaceutically acceptable carrier.

31. A method of treating an animal or human suffering from an inflammatory and/or autoimmune disorder comprising administering thereto an amount effective to treat an inflammatory and/or autoimmune disorder of the compound according to claim 12.

32. The method of claim 31, wherein said administration is oral administration.

33. The method of claim 31, wherein said administration is parental administration.

34. A pharmaceutical composition comprising a compound according to claim 7 and a pharmaceutically acceptable carrier.

35. A method of treating an animal or human suffering from an inflammatory and/or autoimmune disorder comprising administering thereto an amount effective to treat an inflammatory and/or autoimmune disorder of the compound according to claim 7.

36. The method of claim 35, wherein said administration is oral administration.

37. The method of claim 35, wherein said administration is parental administration.

38. A pharmaceutical composition comprising a compound according to claim 1 and a pharmaceutically acceptable carrier.

39. A method of treating an animal or human suffering from an inflammatory and/or autoimmune disorder comprising administering thereto an amount effective to treat an inflammatory and/or autoimmune disorder of the compound according to claim 1.

40. The method of claim 39, wherein said administration is oral administration.

41. The method of claim 39, wherein said administration is parental administration.

42. A pharmaceutical composition comprising a compound according to claim 12 and a pharmaceutically acceptable carrier, wherein said compound is 1,2-O-Isopropylidene-3-O-dodecyl-6-deoxy-6-pyrrolidinyl-α,D-glucofuranose.

43. A method of treating an animal or human suffering from an inflammatory and/or autoimmune disorder comprising administering thereto an amount effective to treat an inflammatory and/or autoimmune disorder of the compound according to claim 12, wherein said compound is 1,2-O-Isopropylidene-3-O-dodecyl-6-deoxy-6-pyrrolidinyl-α,D-glucofuranose.

44. The method of claim 43, wherein said administration is oral administration.

45. The method of claim 43, wherein said administration is parental administration.

* * * * *

UNITED STATES PATENT AND TRADEMARK OFFICE
CERTIFICATE OF CORRECTION

PATENT NO. : 5,360,792
DATED : November 1, 1994
INVENTOR(S) : Sudershan K. ARORA et al.

It is certified that error appears in the above-indentified patent and that said Letters Patent is hereby corrected as shown below:

Claim 6, column 14, line 7, "hexose" should read --hexofuranose--.

Claim 19, column 15, line 62, "hexose" should read --hexofuranose--

Claim 29, column 16, line 53, "parental" should read --parenteral--.

Claim 33, column 16, line 65, "parental" should read --parenteral--.

UNITED STATES PATENT AND TRADEMARK OFFICE
CERTIFICATE OF CORRECTION

PATENT NO. : 5,360,792
DATED : November 1, 1994
INVENTOR(S) : Sudershan K. ARORA et al.

It is certified that error appears in the above-indentified patent and that said Letters Patent is hereby corrected as shown below:

Claim 37, column 17, line 9, "parental" should read --parenteral--.

Claim 41, column 18, line 2, "parental" should read --parenteral--.

Claim 45, column 18, line 18, "parental" should read --parenteral--.

Signed and Sealed this

Fourth Day of April, 1995

BRUCE LEHMAN

Attest:

Attesting Officer

Commissioner of Patents and Trademarks